United States Patent [19]
Suzuki et al.

[11] Patent Number: 5,399,411
[45] Date of Patent: Mar. 21, 1995

[54] FLEXIBLE, AIR-PERMEABLE PLASTIC SHEET

[75] Inventors: Migaku Suzuki; Masamitsu Yamamoto, Kawanoe; Masaki Murakami, Kawanoe, all of Japan

[73] Assignee: Uni-Charm Corporation, Ehime, Japan

[21] Appl. No.: 84,245

[22] PCT Filed: Nov. 6, 1991

[86] PCT No.: PCT/JP91/01520
§ 371 Date: Jul. 1, 1993
§ 102(e) Date: Jul. 1, 1993

[87] PCT Pub. No.: WO/9308780
PCT Pub. Date: May 13, 1993

[51] Int. Cl.⁶ .......................................... D03D 15/00
[52] U.S. Cl. ............................. 428/105; 428/107; 428/131; 428/134; 428/163; 428/167; 428/226; 428/247; 428/255; 428/910
[58] Field of Search ............... 428/105, 107, 131, 134, 428/163, 167, 247, 255, 910, 226

[56] References Cited

U.S. PATENT DOCUMENTS

| | | | |
|---|---|---|---|
| 2,902,037 | 9/1959 | Harwood | 604/365 |
| 4,342,314 | 8/1982 | Radel et al. | 128/287 |
| 4,601,868 | 7/1986 | Radel | 264/504 |
| 4,609,518 | 9/1986 | Curro et al. | 264/504 |
| 4,710,185 | 12/1987 | Sneyd, Jr. et al. | 604/372 |

Primary Examiner—D. S. Nakarani
Attorney, Agent, or Firm—Lowe, Price, LeBlanc & Becker

[57] ABSTRACT

Here is disclosed a flexible and air-permeable plastic sheet comprising a plurality of first direction ribs ($Y_1$, $Y_2$, ... ) each having opposite sides (2, 3) extending in the first direction (Y) and curved downward crossing a plurality of second direction ribs ($X_1$, $X_2$, ... ) each having opposite sides (4, 5) extending in the second direction (X) and curved downward so that each pair of adjacent first direction ribs and each pair of adjacent second direction ribs crossing these first direction ribs define together an air-permeable vacant space. At each crossing ($C_1$, $C_2$, $C_3$, $C_4$), one of the ribs bulges upward and opposite side edges of this rib crosses the top ($T_1$, $T_2$) of the other rib. The plastic sheet of this invention is featured by less gloss and less sticky touch, and preferably used as a topsheet of a disposable hygienic wearable article.

1 Claim, 6 Drawing Sheets

FLEXIBLE, AIR-PERMEABLE PLASTIC SHEET

TECHNICAL FIELD OF THE INVENTION

The present invention relates to a flexible, air-permeable plastic sheet having an appearance like woven fabric.

BACKGROUND OF THE INVENTION

It is well known to provide a flexible thermoplastic sheet inclusive of plastic film with a plurality of fine pores and thereby to make the sheet air-permeable. The porous plastic sheet formed in this manner usually has slimy gloss and sticky touch characterizing the plastic sheet which are disliked by users in some applications of the sheet. To alleviate such gloss and to improve the touch of the sheet, several techniques have already been proposed, for example, the technique by which the sheet surface is embossed to take the gloss off and simultaneously to provide the surface with irregularities and pores, and the technique by which a third ingredient having delustering effect as well as pore forming effect is previously mixed into raw material for the sheet so that desired delustering and pore forming effects may be achieved on a step of sheet production.

However, these well known techniques have not been able to achieve a satisfactory improvement of the plastic sheet particularly for such plastic sheet used as a topsheet of disposable hygienic wearable articles such as a sanitary napkin and a disposable diaper, because said gloss and touch of the topsheet of such hygienic wearable articles, which are destined to be in direct contact with wearer's skin, are decisively disliked. U.S. Pat. No. 4,342,314 discloses a technique to provide a flexible plastic sheet with a fibrous appearance and capillary structure. This technique also intends to alleviate the sticky touch usually characterizing the plastic sheet, but the sheet obtained by this technique is considered to have a smooth surface and rather slimy gloss because of its smoothness.

Accordingly, it is a principal object of the present invention to alleviate said gloss and undesirable touch conventionally characterizing the plastic sheet by providing the plastic sheet with air-permeable vacant spaces defined by ribs crossing one another so that these ribs and vacant spaces may cooperate together to create an appearance like woven fabric.

DISCLOSURE OF THE INVENTION

The object set forth above is achieved, according to the present invention, by flexible, air-permeable plastic sheet having an appearance like woven fabric, said plastic sheet comprising:
a plurality of ribs extending in a first direction, each having opposite side edges curved downward and a plurality of ribs extending in a second direction, each having opposite side edges curved downward so that these first and second direction ribs cross one another to present said appearance like woven fabric;
each pair of adjacent said first direction ribs and each pair of adjacent said second direction ribs crossing these first direction ribs defining together an air-permeable vacant space; and
said pair of first direction ribs bulge upward at first and second crossings which are adjacent and diagonally opposed to each other so that bulgings aligned in the first direction are formed and a pair of lower edges of each said bulging are connected to tops of said pair of second direction ribs, on one hand, and said pair of second direction ribs bulge upward at third and fourth crossings which are adjacent and diagonally opposed to each other so that bulgings aligned in the second direction are formed and a pair of lower edges of each said bulging are connected to tops of said pair of first direction ribs, on the other hand.

According to an aspect of the invention, each of said first and second direction ribs preferably has a hollow arcuate cross-section.

According to another aspect of the invention, each said second direction rib has preferably a width smaller than a width of each said first direction rib at least along a longitudinally intermediate portion of said second direction rib.

According to still another aspect of the invention, said pair of adjacent fist direction ribs are preferably provided with bridges connecting opposite lower edges of these ribs.

Advantageous effect provided by the invention will be readily apparent from the following description.

In the plastic sheet of the invention constructed as has been mentioned above, the first direction ribs cross the second direction ribs and, at each crossing, one of ribs bulges upward so that each rib has undulations between each pair of ribs crossing this rib and creates an appearance corresponding to a texture of plain weave fabric. Provision of said bridges between each pair of adjacent ribs creates an appearance corresponding to a texture of twill weave fabric.

A hollow arcuate cross-section of each rib provides the rib with a cushioning effect and thereby provides the entire plastic sheet with a comfortable bulky touch.

The first and second direction ribs are arranged at different pitches, respectively, to complicate the rib arrangement and thereby to create a complicated appearance of the plastic sheet like woven fabric.

Complicated variation of the plastic sheet surface given by bulgings and undulations of each rib promotes diffused reflection of incident light and thereby effectively alleviates the slimy gloss conventionally characterizing the plastic sheet in general.

Bulgings and undulations on the surface of the plastic sheet effectively reduce the area of the sheet destined to be in contact with wearer's skin and thereby alleviate the sticky touch also conventionally characterizing the plastic sheet.

BEST MODE FOR CARRYING OUT THE INVENTION

Referring to FIGS. 1 through 6, an embodiment of the flexible, air-permeable plastic sheet 1 constructed in accordance with the teachings of the invention is partially illustrated in plan and sectional views, respectively.

Figure 1:
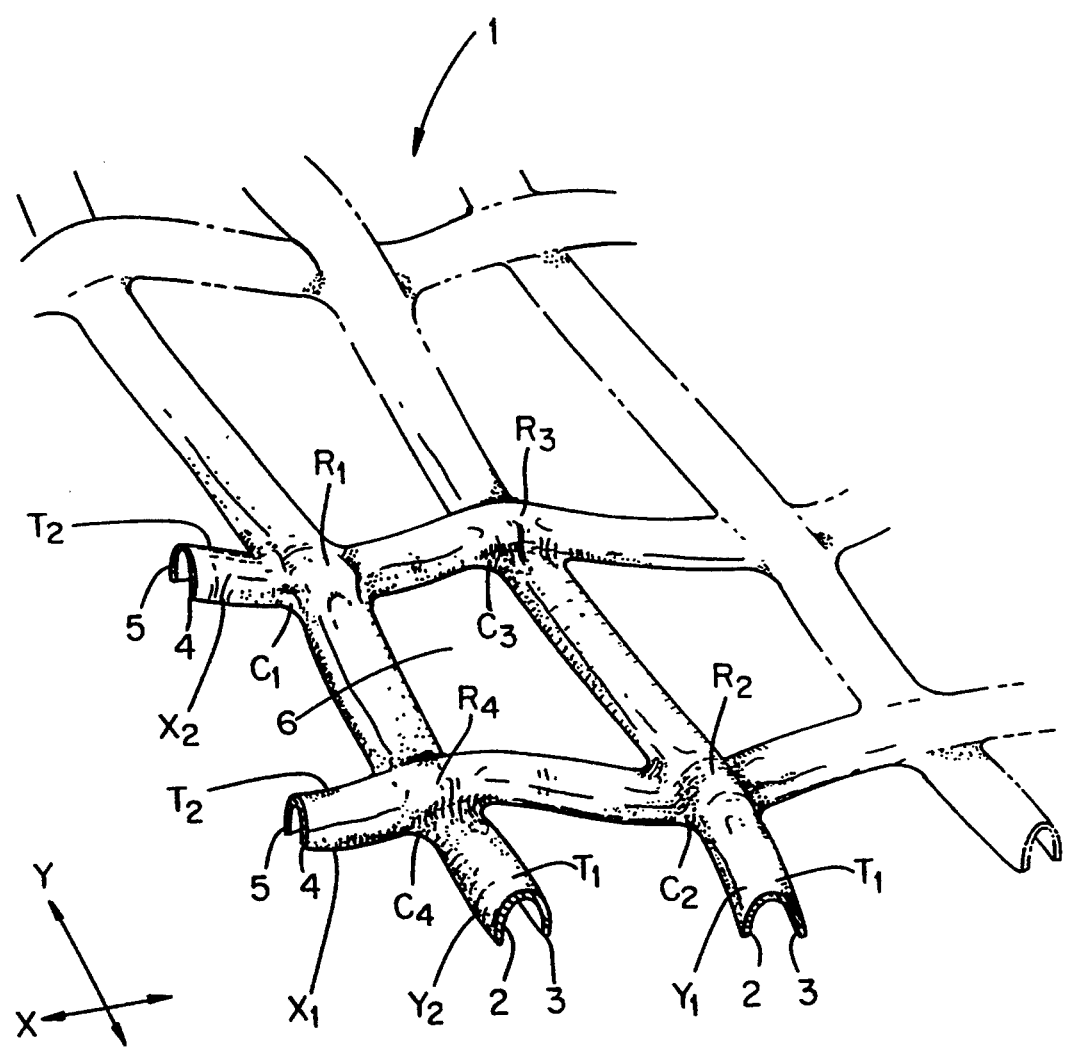
FIGS. 1 through 6 are scale-enlarged perspective, plan and sectional views partially showing an embodiment of a flexible, air-permeable plastic sheet constructed according to the teachings of the invention.

Referring to FIG. 1, solid lines represent the minimum unit of the sheet 1 comprising countless ribs and this unit is repeated in longitudinal and transverse directions to form a complete sheet 1. This unit of the sheet 1 comprises a pair of ribs $Y_1$, $Y_2$ extending in a first direction Y and a pair of ribs $X_1$, $X_2$ extending in a second direction X, these ribs being substantially uniform in their widths. The respective ribs are transversely curved downwardly of the sheet 1 so that the ribs $Y_1$, $Y_2$ have respective pairs of lower edges 2, 3 longitudinally extending in parallel to each other, respectively, and the ribs $X_1$, $X_2$ similarly have respective pairs of lower edges 4, 5 longitudinally extending in parallel to each other, respectively. The pair of adjacent ribs $Y_1$, $Y_2$ extending in the first direction cross the pair of adjacent ribs $X_1$, $X_2$ extending in the second direction at crossings $C_1$ through $C_4$. At the first and second crossings $C_1$, $C_2$ which are adjacent and diagonally opposed to each other, the ribs $Y_1$, $Y_2$ of the first direction bulge upward to form bulgings $R_1$, $R_2$, respectively. Similarly, the ribs $X_1$, $X_2$ of the second direction bulge upward to form bulgings $R_3$, $R_4$, respectively, at the third and fourth crossings $C_3$, $C_4$ which are adjacent and diagonally opposed to each other. At the bulgings $R_1$, $R_2$, the respective pairs of lower edges 2, 3 of the first direction ribs $Y_1$, $Y_2$ are connected to respective tops $T_2$ of the second direction ribs $X_1$, $X_2$ which extend in the second direction. Similarly, at the bulgings $R_3$, $R_4$, the respective pairs of lower edges 4, 5 of the second direction ribs $X_1$, $X_2$ are connected to the respective tops $T_1$ of the first direction ribs $Y_1$, $Y_2$ which extend in the first direction. The ribs $Y_1$, $Y_2$ and the adjacent ribs $X_1$, $X_2$ meet substantially at right angles and these four ribs define together an air-permeable vacant space 6, which is a through hole. The sheet 1 constructed in this manner has an appearance corresponding to that of plain weave fabric.

Figure 2:
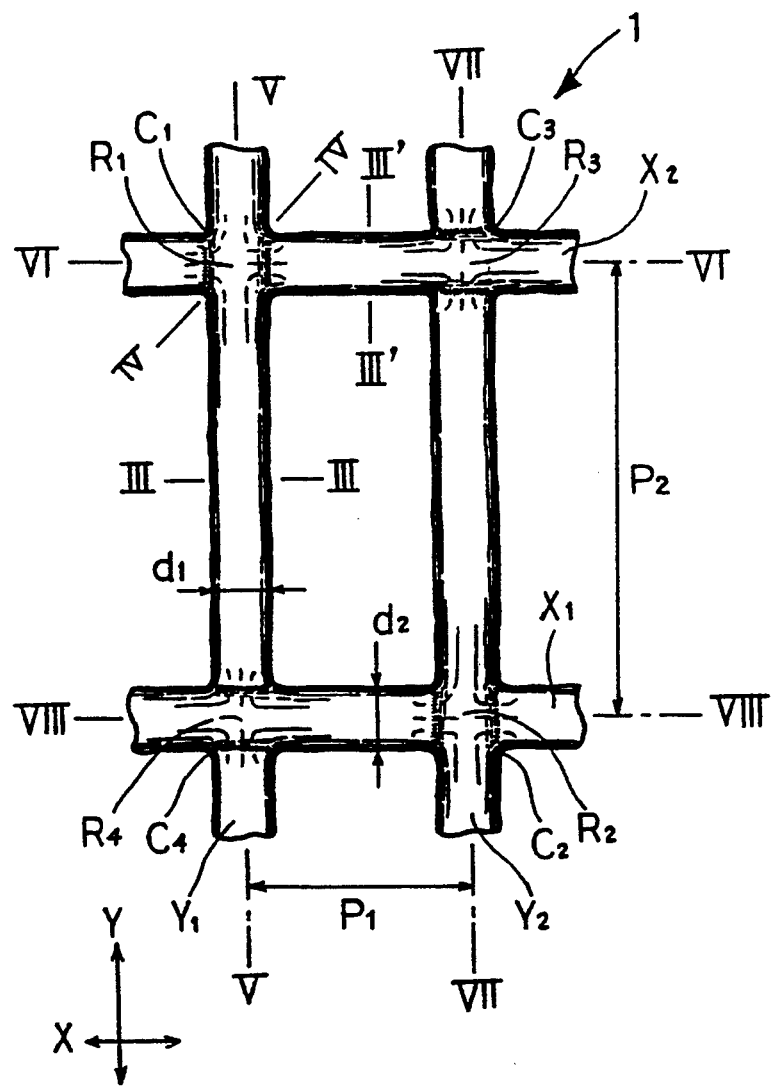

FIG. 2 is a plan view overlooking the sheet 1 shown by FIG. 1. Referring to this figure, the first direction ribs $Y_1$, $Y_2$ have a pitch $P_1$ and the second direction ribs $X_1$, $X_2$ have a pitch $P_2$, wherein $P_1 < P_2$. However, the sheet 1 may be constructed so as to establish a relationship of $P_1 \geq P_2$. In addition, the ribs may obliquely cross one another, instead of crossing at right angles.

The ribs $Y_1$, $Y_2$ have a width $d_1$ and the ribs $X_1$, $X_2$ have a width $d_2$. While this specific embodiment is illustrated as the width $d_1$ is substantially equal to the width $d_2$, any of these $d_1$ and $d_2$ may be larger than the other and each rib may be locally thinned along its longitudinally intermediate portion.

Figure 3:
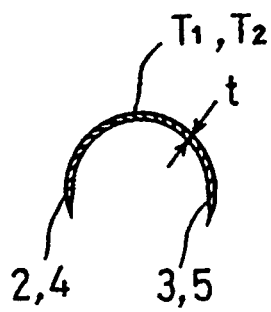

FIG. 3 is a schematic sectional view commonly showing the rib $Y_1$ along a line III—III and the rib $X_2$ along a line III'—III' in FIG. 2. As shown, each rib has a substantially semi-circular cross-section consisting of the top $T_2$ or $T_1$, a substantially uniform thickness t, and the pair of tapered lower edges 2, 3 (on the rib $Y_1$) or 4, 5 (on the rib $X_2$).

Figure 4:
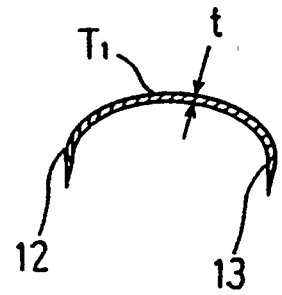

Referring to FIG. 4, the first direction rib $Y_1$ is shown at the crossing $C_1$ in a section taken along a line IV—IV in FIG. 2 extending at an angle of 45° with respect to this rib $Y_1$. The rib $Y_1$ presents a substantially semi-elliptical cross-section including the top $T_1$, the thickness t and a pair of tapered lower edges 12, 13 along which the top $T_2$ and the vicinity thereto are connected to the lower edges 2, 3 of the rib $Y_1$. The cross-sections taken along lines extending at an angle of 45° with respect to the first direction at the other crossings $C_2$ through $C_4$ are substantially identical to that shown by FIG. 4 except the respective ribs defining the bulgings.

Figure 5:
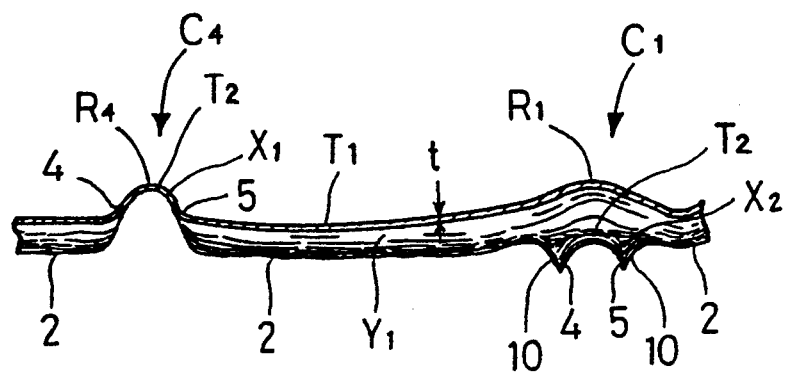

FIG. 5 is a sectional view taken along a line V—V in FIG. 2, and includes sections of the bulgings $R_1$, $R_4$ at the crossings $C_1$, $C_4$, respectively. At the crossing $C_1$, the rib $Y_1$ bulges upward to form the bulging $R_1$ and the lower edge 2 thereof is connected to the top $T_2$ of the rib $X_2$. At the opposite sides of the bulging $R_1$, it will be seen in FIG. 5 that the lower edges 4, 5 of the rib $X_2$ are connected through contours 10 to the lower edge 2 of the rib $Y_1$. At the crossing $C_4$, the rib $X_1$ bulges upward to form the bulging $R_4$ and the lower edges 4, 5 thereof are connected to the top $T_1$ of the rib $Y_1$. It will be apparent also that the rib $Y_1$ has undulations between the ribs $X_1$, $X_2$.

Figure 6:
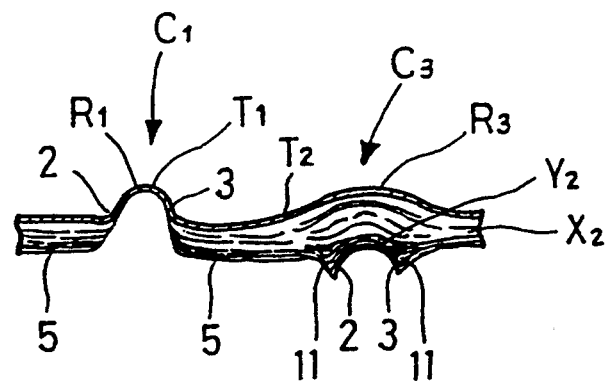

FIG. 6 is a sectional view taken along a line VI—VI in FIG. 2, and includes sections of the bulgings $R_1$, $R_3$ at the crossings $C_1$, $C_3$, respectively. The manner in which the ribs $Y_1$ and $X_2$ bulge upward and are connected to each other at the crossing $C_1$ has already been described in reference with FIG. 5. At the crossing $C_3$, the rib $X_2$ bulges upward to form the bulging $R_3$ and the lower edge 5 thereof is connected to the top $T_1$ of the rib $Y_2$. At the opposite sides of the bulging $R_3$, the lower edges 2, 3 of the rib $Y_2$ are connected through contours 11 to the lower edges 5 of the rib $X_2$.

Sections taken along lines VII—VII and VIII—VIII in FIG. 2, respectively, substantially correspond to FIGS. 5 and 6 laterally reversed, respectively and are not shown for simplicity.

In order that the sheet 1 can have an appearance of woven fabric, the rib width $d_1$, $d_2$ should be 0.01 to 3 mm, more preferably, 0.05 to 2 mm and the number of vacant spaces 6 should be 5 to 90 per 25.4 mm, more preferably, 10 to 60 per 25.4 mm of the respective ribs. The sheet 1 may be made from 5 to 50 g/m$^2$, more preferably, 20 to 30 g/m$^2$ of polyethylene, polypropylene, polyester or other thermoplastic sheets. Improvement of gloss as well as touch and further emphasis of fibrous appearance are effectively achieved by various measures such as rough-surface finishing of the sheet 1 for better diffused reflection of incident light, contouring of each vacant space 6 by irregular curve, irregular variation of the rib width longitudinally thereof, approprite variation of the rib pitch and appropriate coloring of the sheet 1.

Figure 7:
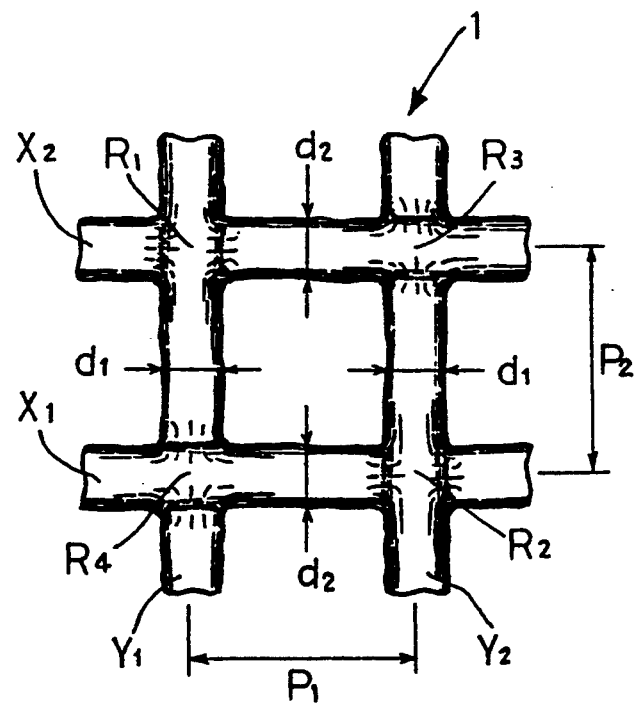
FIGS. 7 and 8 are scale-enlarged fragmentary plan views showing alternative embodiments of such plastic sheet.

Referring to FIG. 7, an alternative embodiment of the invention is shown in a plan view. As illustrated, each rib $Y_1$, $Y_2$ has a width $d_1$ substantially equal to a width $d_2$ of each rib $X_1$, $X_2$ and said rib $Y_1$, $Y_2$ has a pitch $P_1$ substantially equal to a pitch $P_2$ of said rib $X_1$, $X_2$.

Figure 8:
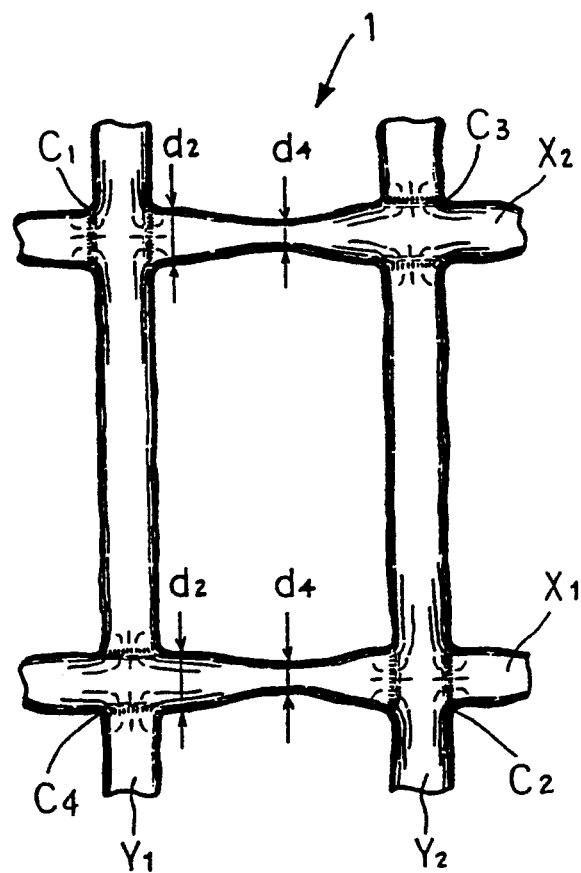

Referring to FIG. 8 further alternative embodiment of the invention is shown also in a plan view. In this specific plastic sheet 1, the widths $d_2$ of the respective ribs $X_1$, $X_2$ continuously vary between the crossings $C_1$ and $C_3$ and between the crossings $C_2$ and $C_4$, respectively. More specifically, the ribs $X_1$, $X_2$ have the most reduced widths $d_4$ at the middle points, respectively.

Figure 9:
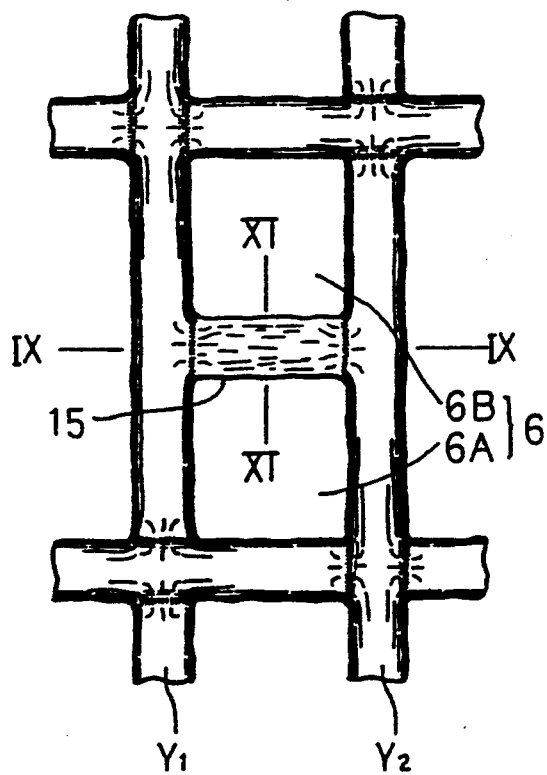
FIGS. 9 through 11 are scale-enlarged fragmentary plan and sectional view showing still another embodiment of such plastic sheet.
Figure 10:
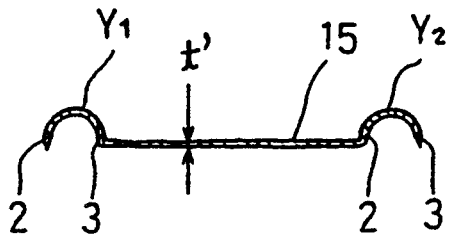
Figure 11:
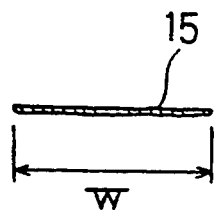

Referring to FIGS. 9 through 11, still another embodiment is shown in plan and sectional views, respectively. As seen in FIG. 9, this plastic sheet 1 includes a bridge 15 connecting the ribs $Y_1$, $Y_2$ to each other. FIGS. 10 and 11 are sectional views taken along lines IX—IX and XI—XI in FIG. 9. The bridge 15 extends between the lower edge 3 of the rib $Y_1$ and the opposed lower edge 2 of the rib $Y_2$, and has a width W and a thickness t'. The width W may irregularly vary between the opposite ends of the bridge 15 and preferably the thickness t' is substantially equal to or smaller than the thickness t of the rib so that the desired flexibility of the sheet 1 may be maintained. It is unnecessary to provide all the vacant spaces 6 with such bridges 15. In this specific embodiment, the bridge 15 presents together with the adjacent ribs an appearance corresponding to that of twill weave fabric.

Figure 12:
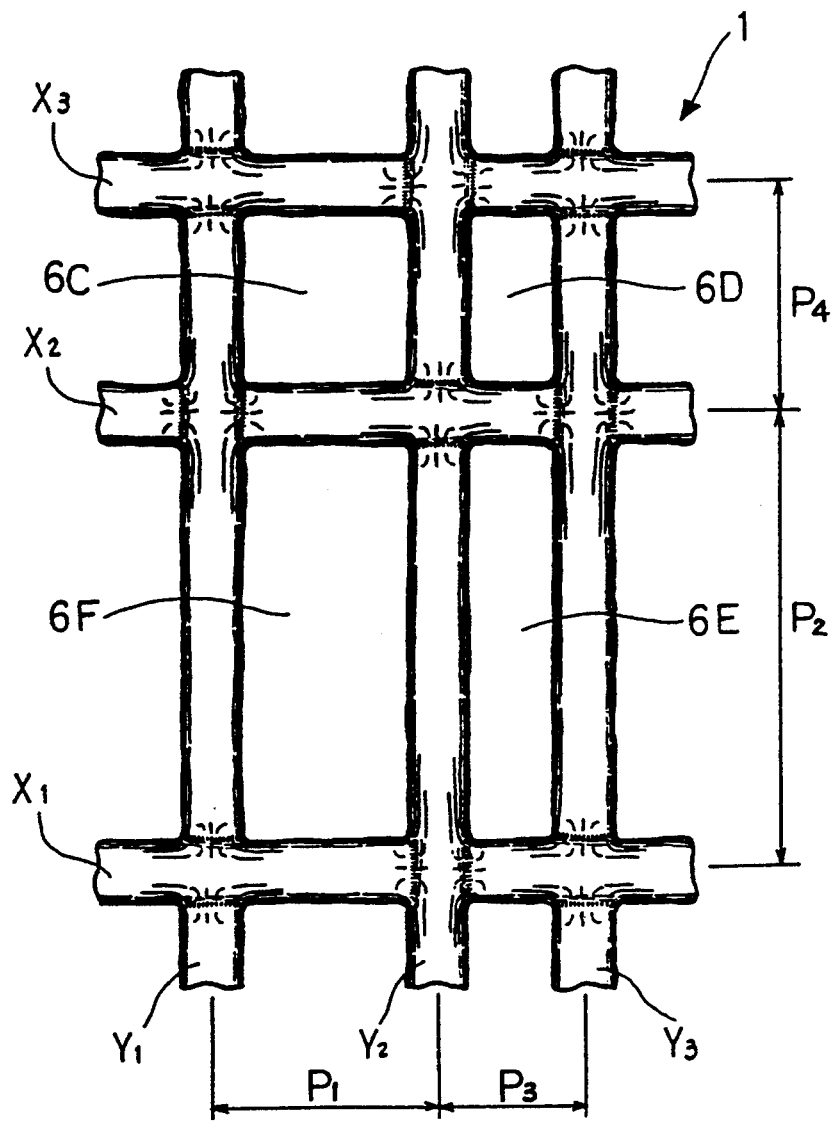
FIG. 12 is a scale-enlarged fragmentary plan view showing further another embodiment of such plastic sheet.

Referring to FIG. 12, further another embodiment is shown in a plan view. The ribs $Y_1$, $Y_2$, $Y_3$ have pitches $P_1$, $P_3$ in the first direction while the ribs $X_1$, $X_2$, $X_3$ have pitches $P_2$, $P_4$, and these pitches are different from one another. In other words, the ribs of the first direction ($Y_1$, $Y_2$, $Y_3$ ...) are arranged at the alternatively repeated pitches $P_1$, $P_3$ and the ribs of the second direction ($X_1$, $X_2$, $X_3$ ...) are arranged at the alternately repeated pitches $P_2$, $P_4$ to form the complete sheet 1.

The plastic sheet 1 may be produced by various methods and one of relatively simple methods is based on a principle of thermoforming comprising steps of placing a plastic sheet, while it is thermally softened, on a top of a wire net which has a texture like plain weave, twill weave, satin weave or the like formed by wire, subjecting the plastic sheet to an effect of vacuum suction provided from an underside of the wire net, and providing said plastic sheet with pores at locations corresponding to meshes of the wire net by rupturing the plastic sheet at said locations under the effect of vacuum suction. For continuous production of the plastic sheet 1, a rotatable drum may be provided around its outer peripheral surface with the wire net, said rotatable drum may be adapted to be subjected to the effect of vacuum suction at predetermined locations on said outer peripheral surface and a roll of material sheet may be continuously dereeled, while the sheet is thermally softened, onto said rotatable drum. The plastic sheet 1 unwound from the drum may be then transversely spread to enlarge the vacant spaces of the pores defined by the ribs, to enlarge the rib widths or to obtain the irregularly varying rib widths. For example, the sheet 1 shown by FIG. 8 may be obtained by spreading the sheet 1 shown by FIG. 1. The sheet may be previously softened by heating, if necessary for said step of spreading. Such method often results in the sheet 1 having a locally uneven configuration and it should be understood that such sheet 1 is also covered by the scope of the invention. Additionally, the wire net may be at least partially formed by stranded wire and the sheet may be pressed against such wire net under the effect of vacuum suction to obtain fine irregularities on the rib surfaces which have been intimate with said stranded wire during said thermoforming.

Figure 13:
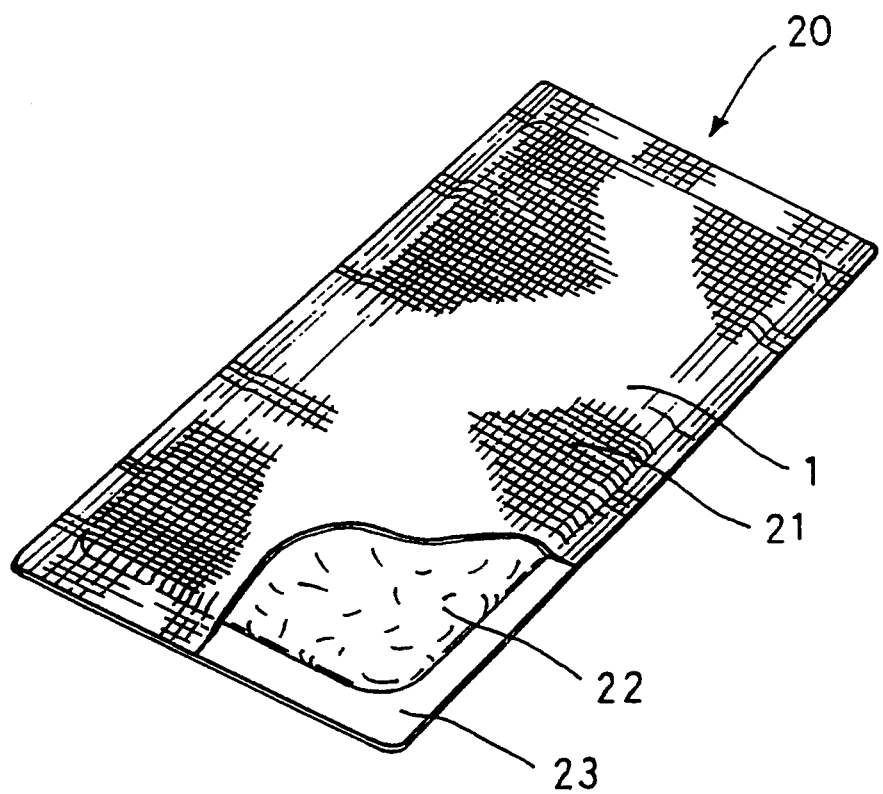
FIG. 13 is a perspective view partially broken away, showing the plastic sheet of the invention exemplarily used on a sanitary napkin.

Referring to FIG. 13, a sanitary napkin 20 utilizing the plastic sheet 1 as a topsheet 21 is shown in a perspective view partially broken away. The napkin 20 comprises an absorbent core 22 adapted to absorb and hold menstrual discharge, an air- and liquid-permeable topsheet 21 and a liquid-impermeable backsheet 23. The topsheet 21 comprises the plastic sheet 1 shown by FIG. 1, the absorbent core 22 comprises a mixture of fluffy pulp and high water absorption polymer powder and the backsheet 23 comprises polyethylene film. The topsheet 21 and the backsheet 23 are bonded together along four edges of the napkin 20 so as to hold back menstrual discharge. The lower edges 2 through 5 of the ribs constituting the plastic sheet 1 are inwardly directed and contacted with the absorbent core 22.

Industrial Usefulness

The plastic sheet constructed in accordance with the teachings of the present invention is industrially useful from the following viewpoints:

1) The sheet has fine bulgings and undulations on its surface on which the diffused reflection of incident light rays occurs to alleviate somewhat slimy gloss conventionally characterizing plastic sheets in general and which reduce an area of the sheet destined to be in contact with a wearer's skin so as to eliminate somewhat sticky touch also conventionally characterizing plastic sheets in general.
2) The sheet presents a surface appearance resembling a texture of woven fabric such as plain weave, twill weave or the like, depending on the pattern of rib arrangement.
3) Each rib is hollow one having the semi-circular cross-section which contributes to provide cushiony and bulky touch.
4) When the sheet of this invention is used as a liquid-permeable topsheet for a disposable hygienic wearing article such as sanitary napkin, the sheet provides a comfortable touch and body fluids discharged onto this sheet will rapidly flow down along the ribs having semi-circular cross-sections through the vacant spaces into an absorbent core so as to prevent the body fluids from stagnating in said topsheet.

We claim:
1. A flexible, air-permeable plastic sheet comprising
(a) a plurality of first ribs extending in parallel in a first direction, each first rib having opposite side edges curved in a downward direction,
(b) a plurality of second ribs extending in parallel in a second direction that is generally perpendicular to said first direction, each of said second ribs having opposite side edges curved in a downward direction,
(c) said first ribs and said second ribs intersecting one another at spaced apart intervals in an over and under sequence to present the appearance of a woven fabric that contains air-permeable vacant spaces;
(d) said first ribs and said second ribs bulging upwardly at their points of intersection,
(e) said first ribs being drawn between their points of intersection with said second ribs so that the portion of said first ribs between said points of intersection significantly narrows in width and is narrower in width than the width of said second ribs between said points of intersection.

* * * * *